( 12 ) United States Patent
Ylikotila et al.

(10) Patent No.: US 8,669,120 B2
(45) Date of Patent: Mar. 11, 2014

(54) HIGH CAPACITY SOLID PHASE

(75) Inventors: Johanna Ylikotila, Raisio (FI); Lasse Välimaa, Lieto (FI); Harri Takalo, Turku (FI); Kim Pettersson, Turku (FI)

(73) Assignee: Innotrac Diagnostics Oy, Turku (FI)

( * ) Notice: Subject to any disclaimer, the term of this patent is extended or adjusted under 35 U.S.C. 154(b) by 325 days.

(21) Appl. No.: 12/503,644

(22) Filed: Jul. 15, 2009

(65) Prior Publication Data

US 2010/0173425 A1 Jul. 8, 2010

(30) Foreign Application Priority Data

Jul. 16, 2008 (DK) ................................. 2008 01003

(51) Int. Cl.
*G01N 33/566* (2006.01)
*G01N 33/543* (2006.01)
*B05D 3/02* (2006.01)

(52) U.S. Cl.
USPC ........................ 436/501; 436/518; 427/372.2

(58) Field of Classification Search
None
See application file for complete search history.

(56) References Cited

U.S. PATENT DOCUMENTS

| | | | |
|---|---|---|---|
| 5,061,640 A | 10/1991 | Tischer et al. | |
| 6,638,728 B1 | 10/2003 | Desai et al. | |
| 2002/0106661 A1* | 8/2002 | Virtanen | 435/6 |
| 2003/0149246 A1 | 8/2003 | Russell | |
| 2007/0202538 A1* | 8/2007 | Glezer et al. | 435/7.1 |

FOREIGN PATENT DOCUMENTS

| | | |
|---|---|---|
| EP | 431169 | 6/1991 |
| EP | 0905517 A1 | 3/1999 |
| WO | WO 99/00670 A1 | 1/1999 |
| WO | WO 99/54735 A1 | 10/1999 |

OTHER PUBLICATIONS

Kernstock et al. "Lipid transfer protein binding of unmodified natural lipids as assessed by surface plasmon resonance methodology" Analytical Biochemistry 365(1):111-121 (2007).

Nilsson et al. "Lipopolysaccharide removal by a peptide-functionalized surface" Colloids and Surfaces. B, Biointerfaces. 40(2):99-106 (2005).

Vikholm-Lundin et al. "Site-directed immobilisation of antibody fragments for detection of C-reactive protein" Biosensors and Bioelectronics 21(7):1141-1148 (2006).

Zuckerman et al. "Sites of arrestin action during the quench phenomenon in retinal rods" FEBS Letters 238(2):379-384 (1988).

International Search Report and Written Opinion issued in PCT Application No. PCT/DK2009/000168 (Nov. 2009).

Holmberg et al., Surfactants and polymers in aqueous solution Holmberg, 1. Introduction to surfactants, pp. 1-37, 2nd Edition, John Wiley & Sons Ltd, West Sussex, England (2003).

Dawson et al., "Spotting optimization for oligo microarrays on aldehyde-glass", Anal. Biochem., 341(2):352-360 (2005).

Diel et al., "Manufacturing DNA microarrays of high spot homogeneity and reduced background signal", Nucl. Acids Res., 29(7): e38, 5 pages (2001).

Preininger et al., "Optimizing processing parameters for signal enhancement of oligonucleotide and protein arrays on ARChip Epoxy", Bioelectrochemistry, 67(2):155-162 (2005).

Rickman et al., "Optimizing spotting solutions for increased reproducibility of cDNA microarrays", Nucl. Acids Res., 31(18): e109, 8 pages (2003).

Valimaa et al., "A high-capacity streptavidin-coated microtitration plate", Bioconjug. Chem., 14(1):103-111 (2003).

Valimaa et al., "Comparison study of streptavidin-coated microtitration plates", J. Immunol. Methods, 308(1-2):203-215 (2006).

Xingfu Chen et al., "Test of 'dry coating' method of ELISA antigen," Chinese Journal of Animal Health Inspection, No. 6, pp. 10-12 (1990).

US 6,200,755, 03/2001, Virtanen (withdrawn)

* cited by examiner

*Primary Examiner* — Shafiqul Haq
*Assistant Examiner* — Galina Yakovleva
(74) *Attorney, Agent, or Firm* — Finnegan, Henderson, Farabow, Garrett & Dunner

(57) ABSTRACT

A high capacity solid phase for bioaffinity assays and other solid phase applications prepared by coating a solid support with an analyte-specific biomolecule in the presence of a zwitterionic additive is described. Structures prepared according to the invention provide high capacity solid phases with enhanced binding properties, which are advantageous for any solid phase based assay.

13 Claims, 6 Drawing Sheets

HIGH CAPACITY SOLID PHASE

FIELD OF THE INVENTION

The present invention relates to a high capacity solid phase for bioaffinity assays and other solid phase applications. The present invention further relates to the use of such high capacity solid phase and a method of preparing it.

BACKGROUND OF THE INVENTION

Solid phase bioaffinity assays are based on the adsorption of antibodies or other biomolecules on a solid support, e.g., on the outer surface of spherical particles, or the inner surface of test tubes, microtitration wells or planar "chip" surfaces, which is then used to immobilize a second capture molecule or an analyte to be detected.

Today, many different coating techniques are known to produce a functionally active surface for solid phase applications. However, current expectations for assay sensitivity, kinetics and robustness set new demands for critical assay components such as the solid phase properties. Existing patterned surfaces are not always able to address the requirements for assay performance and higher surface binding capacity.

The simplest method to produce a solid phase coating is the adsorption of an unmodified protein onto a solid support, which in turn is usually made of polystyrene, polypropylene or some other plastic material or glass. The protein is dissolved in a buffer, e.g., carbonate or phosphate buffer, and applied to the surface of the solid support. The coating is performed in a humid environment, followed by a saturation step to block the unspecific binding sites and finally the surface is dried. However, because usually only a small fraction of the native protein retains its activity after such passive adsorption, the solid phase coating obtained in this way is not always the best choice in terms of binding capacity.

Therefore, several studies have sought to improve adsorption properties and the surface stability of protein coatings, e.g., when the protein is coupled to different "carrier" proteins prior to adsorption to the solid support. Modifications of the native structure of a macromolecule are also often desired to produce improved adsorption properties for demanding assays.

One such macromolecule is streptavidin, which is widely used to capture biotinylated proteins onto a solid phase. The ultimate nature of streptavidin to tightly bind biotin has been utilized in many solid phase-based applications, including microarrays, biosensors and other bioaffinity assays.

U.S. Pat. No. 5,061,640 describes the use of a larger precursor protein to enhance the adsorption of streptavidin. The method provides a coating process which improves the adhesion of the streptavidin to the solid support by conjugating streptavidin to a more hydrophobic carrier molecule like bovine serum albumin prior to coating on a hydrophobic solid support, thus leading to a solid phase with improved binding properties.

Another process to improve the adsorption properties of the coated substances is described in U.S. Pat. No. 6,638,728 B1, which describes the polymerization of monomeric streptavidin with bi-functional linkers to provide a mixture of dimers, trimers and tetramers of streptavidin, which have improved biotin binding capacity compared to a native streptavidin surface when adsorbed onto polystyrene.

The polymerization of thiolated streptavidin through disulphide groups has been shown to provide improvement in the solid phase properties as well, leading to enhanced surface stability by minimizing protein leakage from the solid phase during incubation when coated on polystyrene surfaces (Valimaa, L., Laurikainen, K., 2006: "Comparison-study of streptavidin coated microtitration plates", *J. Immunol. Methods* 308, 203). This study, however, also revealed that although coatings based on thiolated streptavidin showed good solid phase properties and improved binding capacities compared to native streptavidin, other coatings showed higher adsorption capacities. Such coatings, on the other hand, tend to be unstable.

In fact, the solid phase properties are as well highly dependent on the coating conditions used, which in turn includes the buffer composition applied and the coating technique used. Thus, several studies have revealed the importance of the buffer additives in the printing solution to improve spot morphology and reproducibility. In order to reduce the variation between spot morphology and to improve the overall reproducibility of spot production, different surfactants are commonly used.

Thus, with US 2006/0223074 A1, spotting solutions for coating of a solid support comprising an alkylene diol, betaine, a detergent and a salt have been proposed. Betaine (N,N,N-trimethylglycine) has a zwitterionic structure, whereas the detergents disclosed in US 2006/0223074 are ionic or nonionic. Such compositions provide for high spot consistency and stability as well as ease of production and long-term storage.

Several other studies report optimized buffer composition on DNA-microarrays. However, although such studies reported improvement in signal intensity when betaine was used as an additive in the spotting solution, compared to normal spotting solution without additives, rather small total binding capacities were obtained with such coatings.

Thus there still exists a need to provide solid phase coatings for solid supports, wherein the solid phase displays high binding capacities while not compromising the stability properties.

Therefore it is an object of the present invention to provide such high capacity solid phases which may be used for highly efficient applications like microarrays, biosensors and other bioaffinity assays.

SUMMARY OF THE INVENTION

An aspect of the present invention relates to a high capacity solid phase, which is prepared by a method comprising the sequential steps of:
a) coating a solid support with an analyte-specific biomolecule in the presence of a zwitterionic additive, wherein said biomolecule contains an SH-group,
b) incubating the solid support for a period of time sufficient to effect immobilization of said biomolecule to said solid support, and
c) drying said solid support.

Another aspect of the invention is a method for detecting an analyte in a sample, said method comprising the steps of:
i) adding the sample to be tested for content of the analyte to a high capacity solid phase, and
ii) measuring the presence or the concentration of the analyte, wherein the high capacity solid phase is prepared by a method comprising the sequential steps of:
a) coating a solid support with an analyte-specific biomolecule in the presence of a zwitterionic additive, wherein said biomolecule contains an SH-group,
b) incubating the solid support for a period of time sufficient to effect immobilization of said biomolecule to said solid support, and
c) drying said solid support.

Another aspect of the invention is a method of preparing a high capacity solid phase wherein the method comprises the sequential steps of:

a) coating a solid support with an analyte-specific biomolecule in the presence of a zwitterionic additive, wherein said biomolecule contains an SH-group,
b) incubating the solid support for a period of time sufficient to effect immobilization of said biomolecule to said solid support, and
c) drying said solid support.

BRIEF DESCRIPTION OF THE DRAWINGS

The invention is disclosed in more detail by reference to the drawings, although it is understood that the drawings merely represent specific embodiments of the described invention and are not intended to so limit the invention.

DETAILED DESCRIPTION

Figure 1:
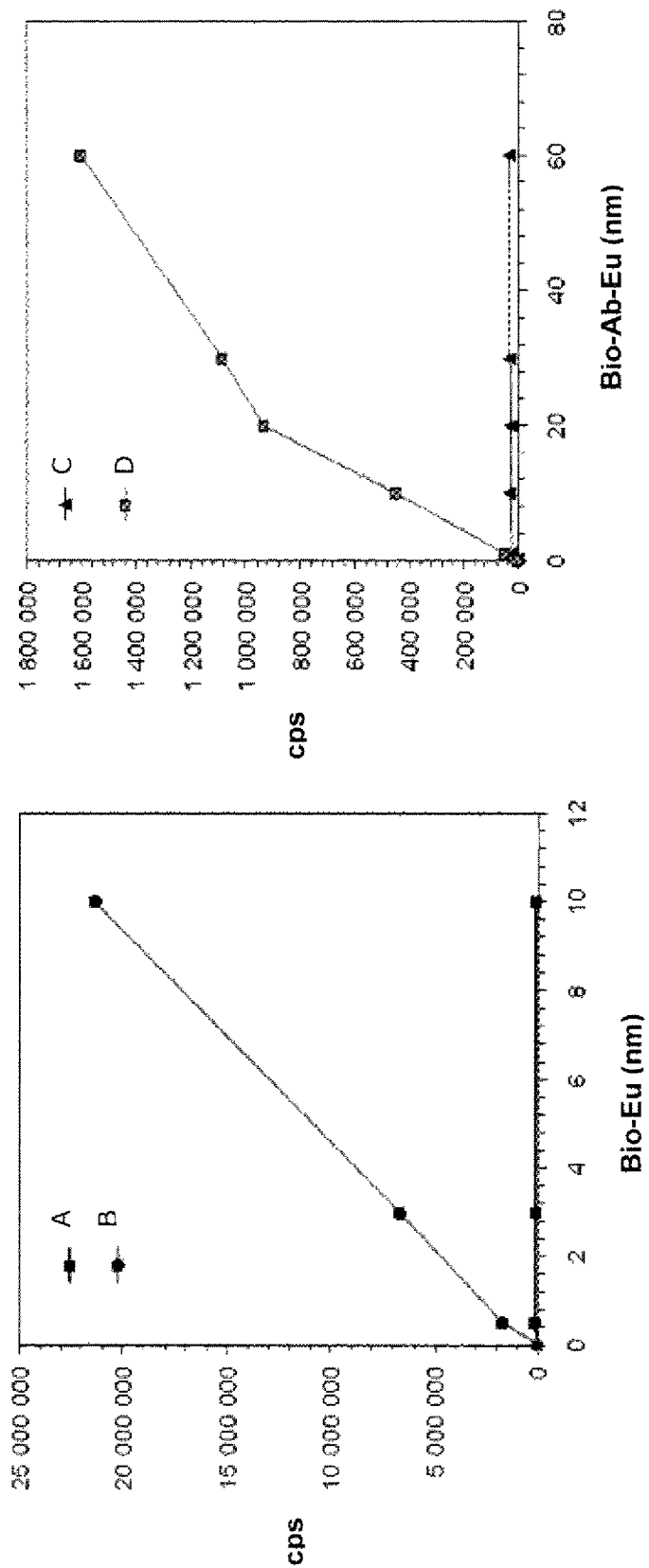
FIG. 1 illustrates the biotin binding capacities of streptavidin-coated spot surfaces using europium labeled biotin and a biotinylated and europium labeled macromolecule, respectively.

In the present context, the term "high capacity solid phase" as used herein refers to any solid phase suitable for the purpose of bioassays.

Further in the present context, the term "solid support" as used herein refers to any solid support suitable for being coated with the above high capacity solid phase. Typically, such solid support may be, for example, but not limited to, a polystyrene, polypropylene or some other plastic material or glass.

The term "analyte-specific biomolecule" as used herein, refers to any biomolecule that has a specific binding capacity for an analyte. It is to be understood that the biomolecule may be specific to the analyte by direct binding, such as when using an antibody as the biomolecule specifically binding the analyte. Alternatively the biomolecule may indirectly bind the analyte, such as the case, for example, when streptavidin is used as a biomolecule that binds a biotin moiety conjugated on the analyte to be measured.

According to the invention, it should be understood that the SH-groups contained in the biomolecule used may be present in the native structure of the biomolecule, e.g., reduced disulphide bonds, or they can be created in the native protein structure by chemical modification.

The term "zwitterionic additive" as used herein, refers to any polar chemical compound that is electrically neutral but carries formal positive and negative charges on different atoms. Examples of zwitterionic additives include, but are not limited to, betaine and phosphorylcholine.

With the high capacity solid phase of the present invention, a new solid phase with surprising highly enhanced binding properties is provided. It has surprisingly been observed that the coating of a solid support with a new innovative coating buffer according to the invention comprising at least one zwitterionic additive as well as at least one biomolecule containing an S—H-group, provides highly increased binding activities compared to conventional coatings when this coating solution is applied in by a dry coating technique. The present coatings surprisingly provide highly enhanced adsorption properties (e.g., up to 100-fold improvement) of the coated substance, thus enabling the production of a high density solid phase with high-capacity binding properties.

In addition hereto an improved spot morphology is observed as is a high stability of the solid phase obtained.

The solid phase according to the invention is obtained by a method wherein the coating is dried during the first incubation, i.e., prior to any saturation step. Such a coating technique is referred to as "dry coating". Dry coating enables a fast coating process which is easy to perform and which shortens the overall time needed for the coating process compared to conventional coating procedures. Dry coating may in turn be applied in terms of ordinary spot coating methods (e.g., for example, drop dispensing and solid pin printing) as well as other printing methods (e.g., for example, inkjet printing).

In some embodiments of the invention, the high capacity solid phase according to the invention is prepared by a method which further comprises a step of saturating the unspecific binding sites on the solid support with a non-interacting moiety.

The term "non-interacting moiety" as used herein, refers to an organic compound or a second biomolecule that does not interact specifically with the biomolecules or analytes used according to the invention, i.e., the non-interacting moiety only binds unspecific binding sites. Typically, such a non-interacting moiety is an inert protein, such as bovine serum albumin, which will bind to unspecific binding sites of the solid support. Further, the non-interacting moiety may bind to unspecific protein sites of the solid phase. Thereby, the signal to noise ratio of specific to unspecific binding is improved and the detection system is made more sensitive to the analyte in question.

The analyte-specific biomolecule according to the invention may be selected from the group consisting of proteins, antibodies, fragments of antibodies, antigens, receptor ligands, protein receptors, specific binding proteins, aptamers, nucleic acids, oligonucleotides, and peptides.

In this context, the term "antibody" as used herein refers to any immunoglobulin or fragment thereof, and encompasses any polypeptide comprising an antigen-binding site. The term includes, but is not limited to, polyclonal, monoclonal, monospecific, polyspecific, non-specific, humanized, human, single-chain, chimeric, synthetic, recombinant, hybrid, mutated, grafted, and in vitro generated antibodies.

With different assays the advantages related to each of these groups of biomolecules are known to the person skilled in the art.

Streptavidin is one generally used biomolecule.

In some embodiments the biomolecule is not a nucleic acid.

In some embodiments of the invention, the biomolecule has been modified by thiolation prior to coating therewith.

It is to be understood that the functional SH-group on a biomolecule may be generated, for example, from reduction of endogenous disulphides bonds within the biomolecule e.g., by enzymatic or chemical cleavage of antibodies or other proteins to release reactive sulphydryl containing antibody fragments. Alternatively a thiolation is performed by any suitable thiolation reagent that creates new thiol groups on the biomolecule.

In one embodiment, an SH-group is already present in the biomolecule.

In one embodiment, the biomolecule has been modified to introduce an SH-group by reduction of an endogenous disulphide bond in the biomolecule.

In one embodiment, the biomolecule has been modified to introduce an SH-group by reduction of a sulphur group already present in the biomolecule.

In some embodiments of the invention, the biomolecule has been modified by thiolation to introduce an SH-group by any suitable thiolation reagent, such as, but not limited to, a thiolation reagent selected from S-acetylthioacetic acid (SATA), 3-(2-pyridyldithio)propionic acid N-hydroxysuccinimide ester (SPDP), N-succinimidyl-S-acetylthiopropionate (SADP), succinimidyloxycarbonyl-α-methyl-α-(2-pyridyldithio)toluene (SMPT), and 2-iminothiolane (Traut reagent).

With such thiolation reagents, efficient and stable thiolation of the biomolecules may be obtained.

In some embodiments of the invention, the zwitterionic additive has the following general structure:

A'-R-A'' wherein,
A' is a group selected from

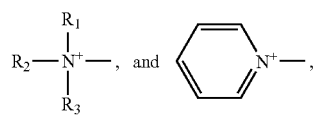

wherein $R_1$, $R_2$ and $R_3$ are independently hydrogen, halogen, —$NO_2$, —CN, —$OR^4$, —$SR^4$, —$SO_2R^4$, —$SOR^4$, $C_{1-6}$-alkyl, $C_{1-6}$-polyfluoroalkyl, $C_{2-6}$-alkenyl, $C_{2-6}$-alkynyl, $C_{3-6}$-cycloalkyl, $C_{2-6}$-alkoxyalkyl, $C_{2-6}$-alkylthioalkyl, or $C_{2-6}$-alkylaminoalkyl, wherein $R^4$ is hydrogen or $C_{1-6}$-alkyl,
R is an alkyl chain of the formula —$(CH_2)_m$—, and m=0–22, and
A'' is a group selected from —$O^-$, —$CO_2^-$, —$OSO_3^{2-}$, —$OPO_3^{2-}$ and —$OPO_3H^-$.

In one specific embodiment, $R_1$, $R_2$ and $R_3$ are independently hydrogen, or the same or different alkyl groups of the formula $CH_3$—$(CH_2)_n$—, and n=0–5.

In some specific embodiments of the invention, $R_1$, $R_2$ and $R_3$ are not hydrogen.

In these embodiments of the invention, the zwitterionic additive has structural similarities with betaine, which provides for efficient and stable coatings.

In some embodiments the zwitterionic additive is selected from betaine and phosphorylcholine. The term "betaine" as used herein refers to the specific compound N,N,N-trimethylglycine.

In some embodiments of the invention, the coating is formed by a coating method selected from a drop-dispensing coating, a solid-pin printing, and an inkjet printing.

Such coating techniques, when applied under the concept of dry coating, allow for highly reproducible coatings to produce the high capacity solid phases of the present invention.

In exemplary embodiments, the methods for coating may also comprise passive adsorption, chemical coupling through functional groups or biochemical interactions.

Another aspect of the present invention relates to the use of the high capacity solid phase according to the invention in a method for solid phase detection of an analyte in a sample, said method comprising the steps of:
a) adding the sample to be tested for content of the analyte to a high capacity solid phase prepared in accordance with the invention, and
b) measuring the presence or the concentration of the analyte.

Methods for the measurement or detection of analytes specifically bound to the high capacity solid phase are known to the person skilled in the art. This may be accomplished by passive means, such as detection of analyte amounts specifically bound to the solid phase e.g., by, for example, but not limited to, measurement of a protein, peptide, amino acid, and/or nucleic acid content by UV absorption using UV spectrophotometry. Alternatively, the analyte is detected or measured by the use of a label present in the detection system. This label may be present, for example, on the analyte, on a partner to the biomolecule or on a second biomolecule binding to the analyte.

The label may be, for example, an endogenous enzymatic member of the analyte itself, or a moiety with enzymatic activity or a radioactive label or any other suitable detectable signal responsive moiety detectable by spectroscopic, optical, photochemical, immunochemical, electrical, calorimetric, or chemical means.

In some embodiments the label is a fluorescent dye. In some embodiments the fluorescent dye is selected from rare earth chelates such as, for example, europium chelates, fluorescein types including FITC, 5-carboxy fluorescein, 6-carboxy fluorescein, rhodamine types including TAMRA, dansyl, lissamine, cyanines, phycoerythrins, Texas Red and analogs thereof.

In some embodiments the label is a radionuclide selected from $^3$H, $^{11}$C, $^{14}$C, $^{18}$F, $^{32}$P, $^{35}$S, $^{64}$Cu, $^{68}$Ga, $^{86}$Y, $^{99}$Tc, $^{111}$In, $^{123}$I, $^{124}$I, $^{125}$I, $^{131}$I, $^{133}$Xe, $^{177}$Lu, $^{211}$At, $^{213}$Bi, and $^{51}$Cr.

In some embodiments according to the invention, the label is present on the analyte, on a partner to the biomolecule of the solid phase or on a second biomolecule binding to the analyte.

The advantages related to each of these embodiments are known to the person skilled in the art.

In some embodiments of the invention, the analyte has been made specific to the biomolecule by conjugating the analyte to a binding partner for the biomolecule.

In a particular embodiment of the invention the binding partner is biotin and the biomolecule is selected from avidin and streptavidin. Alternatively, in another particular embodiment, the binding partner is selected from avidin and streptavidin and the biomolecule is biotin.

In some embodiments of the invention, the biomolecule is an antibody or antibody fragment specific to an antigen, the antigen being the binding partner.

In some embodiments of the invention, the analyte binds directly and specifically to the biomolecule. In some embodiments the biomolecule is an antibody or antibody fragment, which specifically binds to the analyte.

The advantages related to each of the embodiments are known to the person skilled in the art. Thus, each of the embodiments under the present invention provides for highly efficient use of the high capacity solid phase.

According to a third aspect of the invention, a method is provided of preparing a high capacity solid phase wherein the method comprises the sequential steps of:
a) coating a solid support with an analyte-specific biomolecule in the presence of a zwitterionic additive, wherein said biomolecule contains an SH-group,
b) incubating the solid support for a period of time sufficient to effect immobilization of said biomolecule to said solid support, and
c) drying said solid support.

EXAMPLES

The following non-limiting examples illustrate the present invention.

Example 1

Preparation of Thiolated Streptavidin and Coating by Contact Printing

Streptavidin (4 mg) was dissolved in phosphate buffer (50 mM $NaH_2PO_4/Na_2HPO_4$, pH 7.5) to a final concentration of 148 µM. Bifunctional crosslinker N-hydroxysuccinimide ester of S-acetylthioacetic acid (SATA) was dissolved in dimethylformamide and then introduced to the reaction to provide 30-fold molar excess of SATA over streptavidin. The reaction was incubated at room temperature for 30 minutes. After the incubation, the protected thiol groups incorporated with the protein amines were deprotected with 50 mM hydroxylamine for 2 hours. The final product containing thiolated streptavidin was then purified through a desalting column and eluted in 50 mM borate buffer (pH 8.3) containing 1 mM EDTA. The presence of the unpaired thiols was verified using an Ellman's reaction and an average of 10-12 incorporated thiols were regularly found per molecule of streptavidin.

The above thiolated streptavidin was diluted in a coating buffer (100 mM $Na_2HPO_4$/50 mM citric acid, 0.5 M betaine) to a concentration of 1.5 mg/ml and used for the preparation of high capacity coatings on polystyrene microtitration wells. The solution was applied using a solid pin printing technique utilizing 2.0 mm solid pins. After the printing, the wells with the printed spots were incubated and dried over night at +35° C. After the over night incubation, the wells were washed with a washing solution (5 mM Tris-HCl (pH 7.75), 9 g/l NaCl, 1 g/l Germall II and 0.05 g/l Tween 20) and saturated for 2-20 hours at room temperature using a blocking solution containing 50 mM Tris-HCl (pH 7.0), 150 mM NaCl, 0.5 g/l $NaN_3$, 60 g/l D-sorbitol and 2 g/l bovine serum albumin. After the saturation, the wells were dried for 5 hours in a fume hood before use.

The biotin binding capacity (i.e., immobilization efficiency) of the spot wells was determined using two reporter molecules: Europium-labeled biotin (Bio-Eu) and monoclonal antibody bearing biotin and europium-label (Bio-Mab-Eu). The small size of Bio-Eu enables binding to sterically hindered sites and thus it simulates the total biotin binding capacity. Serial dilutions of Bio-Eu (from 0.2 nM to 10 nM) and Bio-Mab-Eu (from 0.1 nM to 60 nM) were prepared in assay buffer (Innotrac buffer solution red from Innotrac Diagnostics, Turku, Finland) and added to the wells at a volume of 50 µl/well. The wells were incubated for one hour at room temperature with shaking, after which they were washed six times with 5 mM Tris-HCl (pH 7.75) containing 9 g/l NaCl, 1 g/l Germall II and 0.005 g/l Tween 20. After drying under a hot air flow (60° C.) for 5 minutes, the time-resolved fluorescence intensity was measured directly from the bottom of the dried wells using a Victor multilabel counter (PerkinElmer Life Sciences—Wallac Oy, Turku, Finland).

FIG. 1 shows the fluorescence signal in counts-per-second (cps) relative to the concentration of Bio-Eu (in the figure "Bio-Eu") and Bio-Mab-Eu (in the figure "Bio-Ab-Eu"), respectively. With both of Bio-Eu and Bio-Mab-Eu, the above modified (thiolated and betaine treated) (B and D, respectively) streptavidin is compared to native streptavidin (A and C, respectively). Thus, in comparison to the spot surfaces prepared with regular chemistry (i.e., native streptavidin without thiol derivatization and betaine addition in the coating solution), the binding capacity of the spot wells described in this example 1 was up to 100 times higher for Bio-Eu and about 40 times higher for Bio-Mab-Eu macromolecule. When phosphorylcholine was used as the surfactant, the binding capacity of the streptavidin surface was increased up to a 100-fold for Bio-Eu and for Bio-Mab-Eu up to a 30-fold improvement in the binding capacity was obtained (not shown).

Example 2

Use of Betaine and Protein Thiolation in a Coating Solution to Improve the Binding Capacity of Streptavidin-coated Regular C-format Microtitration Wells This example illustrates the use of betaine as a coating additive for coatings prepared in the ordinary C-format microtitration wells using a coating volume of 200 µl. The illustrated experiment compares the binding capacity of the coated streptavidin plates prepared with unmodified and thiolated streptavidin, coated with or without additional betaine.

Streptavidin was diluted in a coating buffer (100 mM $Na_2HPO_4$/50 mM citric acid with or without an additional 0.5 M betaine) to a final concentration of 5 µg/ml and added to the microtitration wells (Maxisorp microtitration wells, NUNC A/S, Denmark) at a volume of 200 µl/well. The wells were incubated over night at +35° C. The coating solution was allowed to dry during the over night incubation. Next day the wells were washed with the washing solution and saturated over night at room temperature as described in Example 1. The saturation solution was aspirated and the wells were dried in a fume hood for a few hours (2-5 h).

The biotin binding capacities of the wells were measured with europium labeled biotin. Bio-Eu was diluted in the assay buffer (Innotrac buffer solution red) at concentrations of 0.1 and 1 µM and added to the streptavidin coated wells in a volume of 200 µl/well. Otherwise the test was performed using the protocol described in Example 1.

Figure 2:
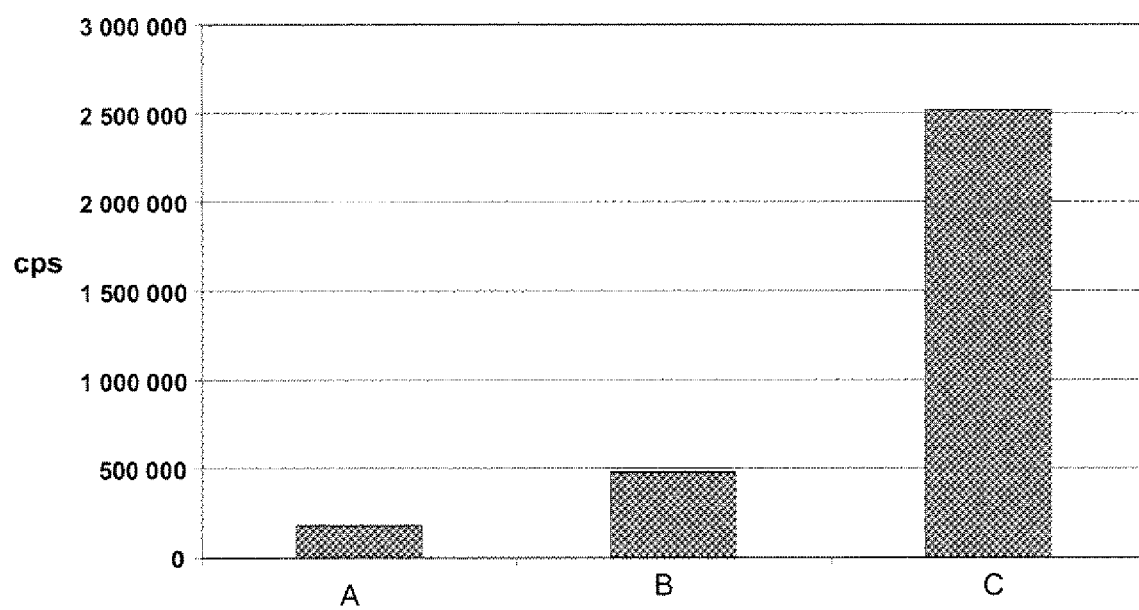
FIG. 2 illustrates the biotin binding capacities of streptavidin coated C-format microtitration wells prepared with unmodified streptavidin with or without an additive in the coating solution or with thiolated streptavidin and an additive in the coating solution.

FIG. 2 shows the binding capacities (measured by fluorescence in cps) of A (native streptavidin), B (native streptavidin and betaine), and C (thiolated streptavidin and betaine). The streptavidin plates coated with additional betaine provided a 3-fold improvement in the biotin binding capacity. Furthermore, a 14-fold improvement in the binding capacity was obtained when thiolated streptavidin was used together with the betaine in the coating solution.

Example 3

Use of Betaine and Protein Thiolation in Coatings to Improve the Binding Capacity of the Streptavidin Coated Spot Wells Prepared by Drop Dispensing Method This example illustrates the use of a different spotting method than the solid pin printing to prepare spot wells with enhanced binding capacity. The spot wells are prepared by pipetting a volume of 4 µl of a coating solution in the middle of the microtitration well bottom (i.e., the drop dispensing method). The binding capacity of the high capacity spot surface prepared using the thiolated streptavidin and the coating solution with the additive is compared with a reference spot surface of unmodified streptavidin.

Streptavidin was modified to contain thiols using the protocol described in Example 1. The thiolated streptavidin was dissolved in the coating buffer (containing 0.5 M betaine) at a final concentration of 1.5 mg/ml. 4 µl of the thiolated streptavidin solution was applied to the bottom of a microtitration well using a regular pipette (Finn pipette). The coating conditions used were the same as described in Example 1. The biotin binding capacity of the coated wells was measured with Bio-Eu, using the protocol described in Example 1.

Figure 3:
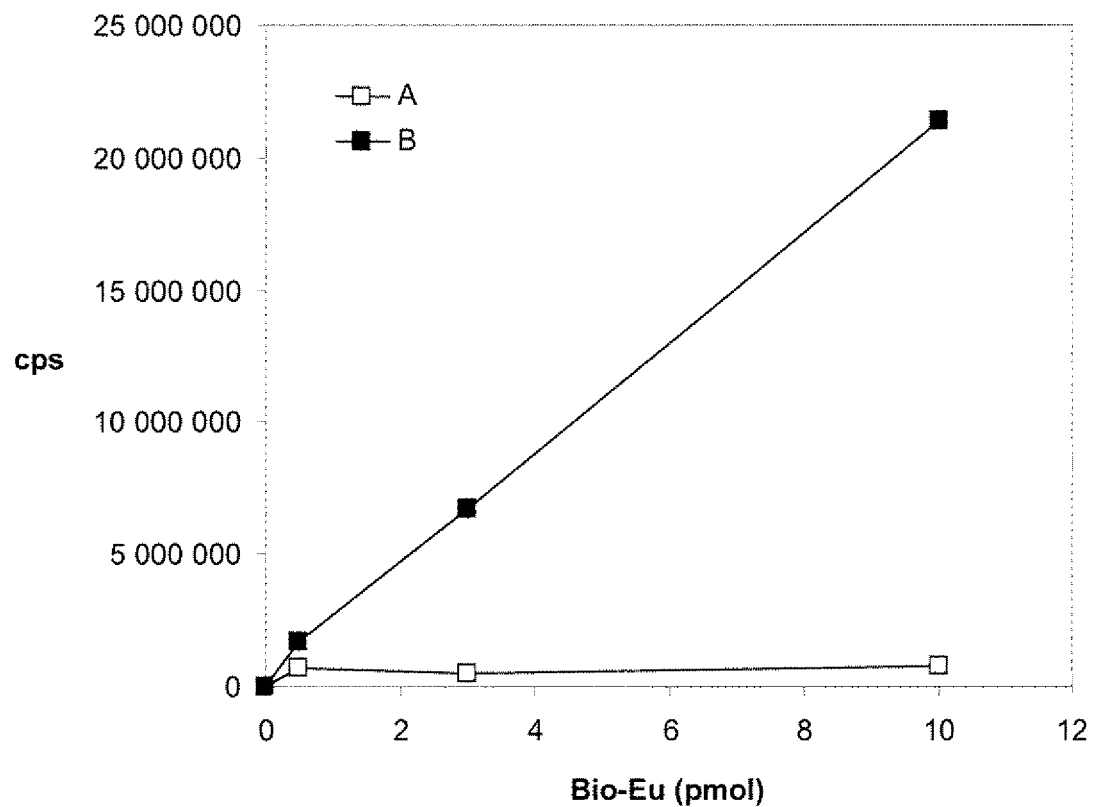
FIG. 3 illustrates the biotin binding capacity of thiolated streptavidin coated spot wells prepared with the drop dispensing method compared to unmodified streptavidin.

FIG. 3 shows the binding capacities (measured by fluorescence in cps) of A (native streptavidin) and B (thiolated streptavidin and betaine). In comparison to the spot wells prepared with native streptavidin, the thiol-modified streptavidin coated with additional betaine exhibited at least a 27-fold improvement in the biotin binding capacity.

Example 4

Use of Betaine and Protein Thiolation in Antibody Coating on Spot Surfaces Prepared by Contact Printing This example illustrates the use of betaine as a coating additive in antibody coatings performed with the contact printing technique. The illustrated assays compare the immobilization efficiency of the high capacity SH-modified monoclonal antibody surface prepared with additional betaine to the immobilization efficiency of the reference surface prepared without additional betaine.

Monoclonal antibody (anti-cTnI monoclonal antibody) was modified with SATA reagent to incorporate additional thiols in the protein. 2 mg of monoclonal antibody was dissolved in phosphate buffer (50 mM $NaH_2PO_4/Na_2HPO_4$; pH 7.5) at a final concentration of 28 µM. SATA was dissolved in dimethylformamide and introduced to the reaction providing a 50-fold molar excess of SATA over the monoclonal antibody. After 30 minutes of incubation, the formed protected thiols incorporated on the antibody were deprotected with 50 mM hydroxylamine for 2 hours. The reaction mixture was then purified through a desalting column and the product, thiolated monoclonal antibody, was eluted in a 0.1 M sodium phosphate buffer (pH 7.2) containing EDTA.

The thiolated antibody was diluted in the coating buffer at a concentration of 0.5 mg/ml and applied to the bottom of the microtitration well (Maxisorp, NUNC A/S, Denmark) with contact printing, using solid pins of 2.0 mm in diameter. The coated spot wells were further treated as described in Example 1. The performance in the immunoassay of the coated wells was measured using a cTnI-immunoassay. Serial dilutions of cTnI antigen were prepared in 7.5% BSA-TSA buffer (50 mM Tris-HCl, pH 7.75; 154 mM NaCl; 0.05 g/l $NaN_3$; 75 g/l BSA) at concentrations of from 0.001 to 800 ng/ml. 20 µl of tracer antibody (anti-cTnI monoclonal antibody labeled with europium, which binds to different epitopes of cTnI than the solid phase antibody) together with 20 µl of standard dilution were added to the coated spot wells and incubated for one hour at +36° C. with shaking (900 rpm). After one hour incubation, the wells were washed 6 times with a washing solution and dried under hot air flow (+60° C.) for 5 minutes before signal measurement. Time resolved fluorescence signal was measured directly from the dried well bottom with a Victor multilabel counter.

Figure 4:
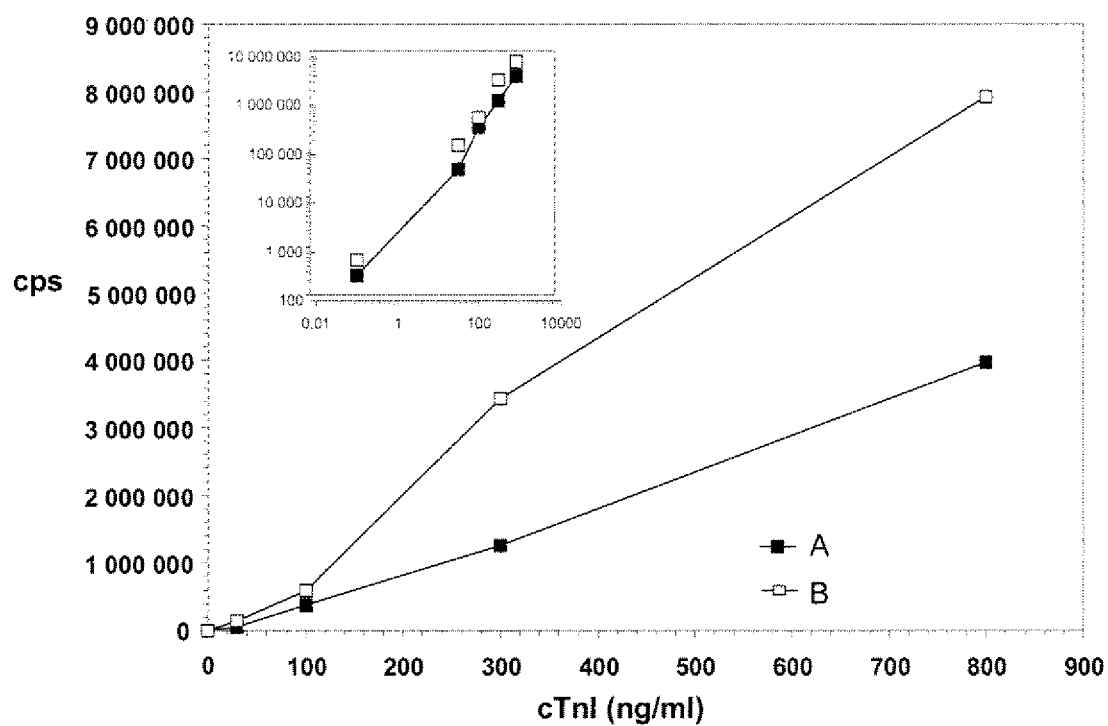
FIG. 4 shows the use of protein thiolation together with the use of betaine as an additive in a coating solution to provide improved surface properties in antibody coatings on polystyrene with a native antibody or with a thiolated antibody, obtained after addition of cTnI and an europium labeled tracer antibody.

FIG. 4 shows the cTnI immunoassay signals (fluorescence measured in cps) of A (normal antibody) and B (thiol-modified and betaine-treated antibody). The wells coated with thiolated antibody and with additional betaine provided up to 66% improvement in the specific signal levels (background signal subtracted) in the cTnI immunoassay, compared to the reference surface.

Figure 5:
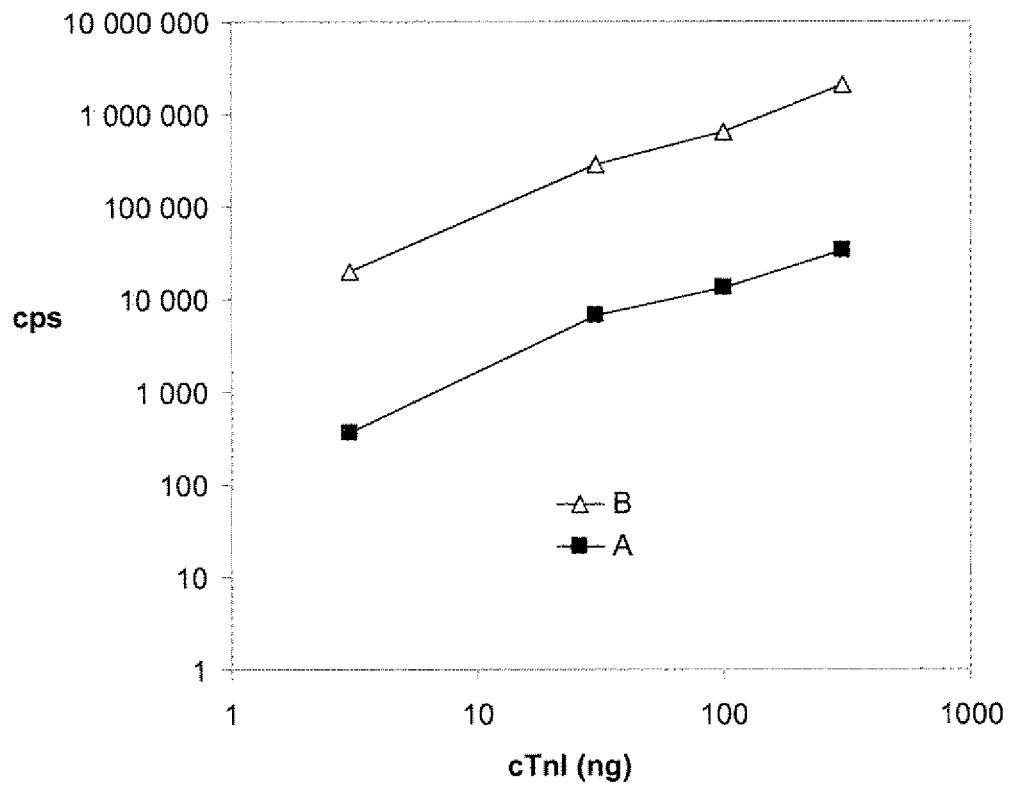
FIG. 5 illustrates the use of a thiolated fragment antibody together with betaine in the coating solution on antibody coatings prepared with a contact printing technique on polystyrene.

Furthermore, the use according to a similar procedure as above of thiolated fragment antibody together with betaine in the coating solution provided a 50- to 60-fold improvement of the surface binding capacity for cTnI compared to the surface coated with native fragment antibody in a coating solution without betaine. This is shown in FIG. 5, in which the cTnI assay signals (in cps) of A (normal fragment antibody) and B (thiol-modified and betaine-treated fragment antibody) are displayed.

Example 5

Use of High Capacity Streptavidin Coating (Thiolated Streptavidin and Betaine) in Capturing of Biotinylated Oligonucleotides The spot coated surfaces of thiolated streptavidin with betaine addition were prepared with the contact printing method as described in Example 1. As a reference surface, spot coated wells prepared with thiolated streptavidin without betaine addition were used. The reference wells were prepared with the contact printing method in the same way as the high capacity surfaces, although no betaine addition was used.

Biotinylated oligonucleotides were diluted in an assay buffer (containing additional 1M NaCl) at concentrations of 0.0002, 0.0001, 0.002, 0.01, 0.02, and 0.04 µmol/µl and applied to the spot surfaces in a volume of 50 µl/spot well. The wells were incubated with slow shaking for 30 min at RT and after incubation, the wells were washed twice with a washing solution (5 mM Tris-HCl (pH 7.75), 9 g/l NaCl, 1 g/l Germall II and 0.05 g/l Tween 20). Terbium (Tb) labeled secondary oligonucleotide was diluted in the assay buffer at concentration of 0.03 µmol/µl and applied to the spot wells. The wells were incubated for 1.5 h at 35° C. with shaking (900 rpm) and after incubation the wells were washed 4 times with the washing solution. After 20 min of Delfia enhancement, the terbium derived signal was measured with time-resolved fluorometry.

Figure 6:
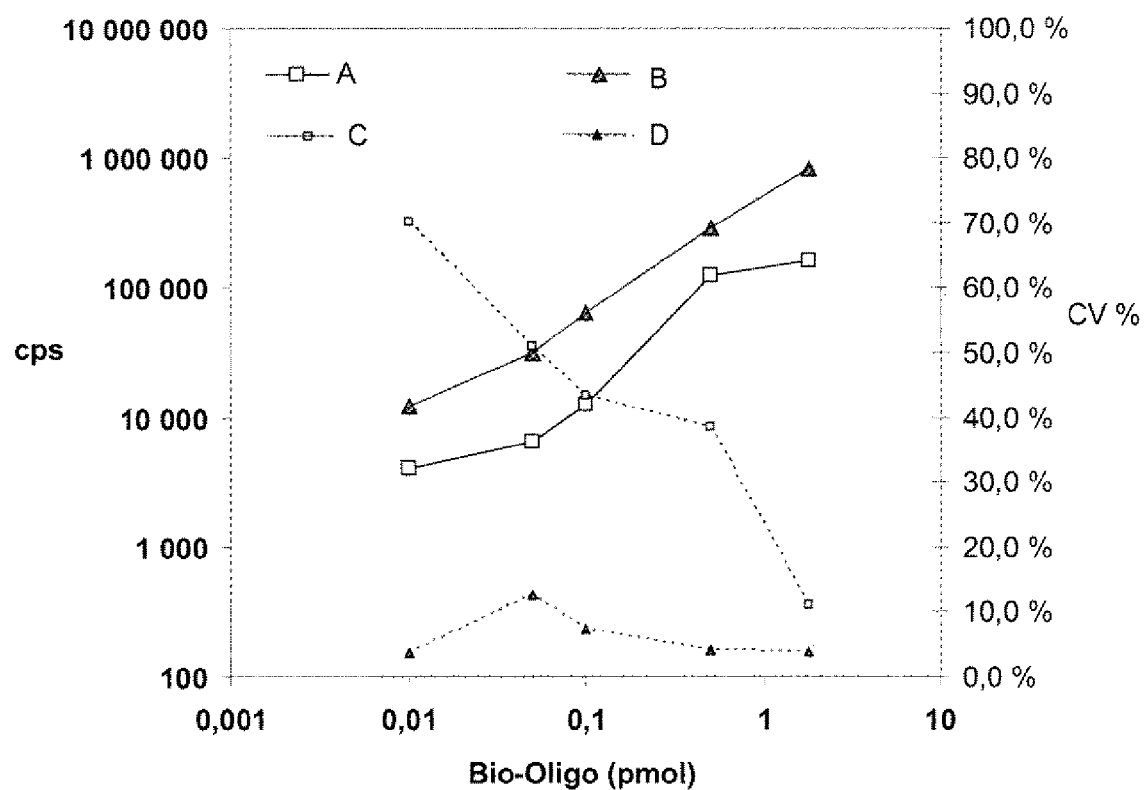
FIG. 6 shows fluorescence derived specific signals from oligonucleotide assays performed at high capacity spot surfaces and at a reference spot surface manufactured with a contact printing technique.

FIG. 6 shows the assay signals (fluorescence measured in cps) of A (oligonucleotide capture with thiolated streptavidin) and B (oligonucleotide capture with thiol-modified and betaine-treated streptavidin). Further, FIG. 6 shows the inter-sample variation (i.e., CV % values, n=3) for A (C) and for B (D).

The spot surfaces prepared with thiolated streptavidin with betaine addition provided clear improvement in the specific signals obtained in the oligonucleotide assay, compared to the spot surfaces prepared with thiolated streptavidin without betaine addition. Up to 5-fold improvement in the specific Terbium-derived signal was obtained with the high capacity coating compared to the reference coating. In addition to the improved specific signal levels, the use of high capacity spot coatings clearly reduced the variation between the replicate wells.

Without further description, it is believed that one of ordinary skill in the art can, using the preceding description and the illustrative examples, make and utilize the present invention and practice the claimed methods. All patents, patent applications and other references cited throughout this application are herein incorporated by reference in their entirety.

The invention claimed is:

1. A high capacity solid phase prepared by a method comprising the sequential steps of:
   a) applying a coating solution on a solid support, wherein said coating solution comprises an analyte-specific biomolecule in the presence of a zwitterionic additive, wherein said biomolecule contains an SH-group,
   b) incubating and drying the solid support for a period of time sufficient to effect immobilization of said biomolecule to said solid support, and
   c) saturating unspecific binding sites on the solid support with a non-interacting moiety.

2. The solid phase according to claim 1, wherein the analyte-specific biomolecule is selected from the group consisting of proteins, antibodies, fragments of antibodies, antigens, receptor ligands, protein receptors, specific binding proteins, aptamers, nucleic acids, oligonucleotides and peptides.

3. The solid phase according to claim 1, wherein the analyte-specific biomolecule is streptavidin.

4. The solid phase according to claim 1, wherein the SH-group on said biomolecule has been introduced by a thiolation reagent selected from the group consisting of S-acetylthioacetic acid (SATA), 3-(2-pyridyldithio)propionic acid N-hydroxysuccinimide ester (SPDP), N-succinimidyl-5-acetylthiopropionate (SADP), succinimidyloxycarbonyl-α-methyl-α-(2-pyridyldithio)toluene (SMPT), and 2-iminothiolane (Traut reagent).

5. The solid phase according to claim 1, wherein the zwitterionic additive has the following general structure:

wherein,

A' is a group selected from the group consisting of

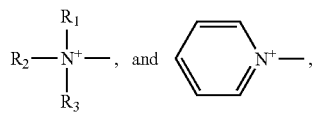

wherein $R_1$, $R_2$ and $R_3$ are independently hydrogen, halogen, —$NO_2$, —CN, —$SR^4$, —$SO_2R^4$, —$SOR^4$, $C_{1-6}$-alkyl, $C_{1-6}$-polyfluoralkyl, $C_{2-6}$-alkenyl, $C_{2-6}$-alkynyl, $C_{3-6}$-cycloalkyl, $C_{2-6}$-alkoxyalkyl, $C_{2-6}$-alkylthioalkyl, or $C_{2-6}$-alkylaminoalkyl, wherein $R^4$ is hydrogen or $C_{1-6}$-alkyl, R is an alkyl chain of the formula —$(CH_2)_m$—, wherein m 0-22, and A" is a group selected from the group consisting of —$O^-$, —$CO_2^-$, —$OSO_3^-$, —$OPO_3^{2-}$ and —$OPO_3H^-$.

6. The solid phase according to claim 5, wherein $R_1$, $R_2$ and $R_3$ are independently hydrogen, or the same or different alkyl groups of the formula $CH_3$—$(CH_2)_n$—, wherein n=0–5.

7. The solid phase according to claim 1, wherein the coating step is performed by a coating method selected from the group consisting of a drop-dispensing coating, a solid-pin printing, and an inkjet printing.

8. A method for detecting an analyte in a sample, said method comprising the steps of:
   i) adding the sample to be tested for content of the analyte to a high capacity solid phase, and
   ii) measuring the presence or the concentration of the analyte, wherein the high capacity solid phase is prepared by a coating method comprising the sequential steps of:
   a) applying a coating solution on a solid support, wherein said coating solution comprises an analyte-specific biomolecule in the presence of a zwitterionic additive, wherein said biomolecule contains an SH-group,
   b) incubating and drying the solid support for a period of time sufficient to effect immobilization of said biomolecule to said solid support, and
   c) saturating unspecific binding sites on the solid support with a non-interacting moiety.

9. The method according to claim 8, wherein the analyte is measured by detection of a label present on the analyte, on the partner for the biomolecule or on a second biomolecule binding to the analyte.

10. The method according to claim 8, wherein the analyte is conjugated to a binding partner for said biomolecule.

11. The method according to claim 10, wherein the binding partner is biotin and the biomolecule is selected from the group consisting of avidin and streptavidin.

12. The method according to claim 10, wherein the biomolecule is an antibody or antibody fragment specific to an antigen, the antigen being the binding partner.

13. A method of preparing a high capacity solid phase wherein the method comprises the sequential steps of:
   a) applying a coating solution on a solid support, wherein said coating solution comprises an analyte-specific biomolecule in the presence of a zwitterionic additive, wherein said biomolecule contains an SH-group,
   b) incubating and drying said solid support for a period of time sufficient to effect immobilization of said biomolecule to said solid support, and
   c) saturating unspecific binding sites on the solid support with a non-interacting moiety.

* * * * *